United States Patent
Kerr et al.

(10) Patent No.: US 8,771,721 B2
(45) Date of Patent: *Jul. 8, 2014

(54) FLEXIBLE BONE COMPOSITE

(71) Applicant: Depuy Synthes Products, LLC, Raynham, MA (US)

(72) Inventors: Sean Kerr, Oreland, PA (US); James W. Dwyer, West Chester, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/838,629

(22) Filed: Mar. 15, 2013

(65) Prior Publication Data

US 2013/0209526 A1    Aug. 15, 2013

Related U.S. Application Data

(63) Continuation of application No. 13/539,779, filed on Jul. 2, 2012, now Pat. No. 8,420,108, which is a continuation of application No. 13/208,837, filed on Aug. 12, 2011, now Pat. No. 8,221,782, which is a continuation of application No. 11/148,193, filed on Jun. 9, 2005, now Pat. No. 8,012,501.

(60) Provisional application No. 60/578,610, filed on Jun. 10, 2004.

(51) Int. Cl.
*A61K 33/42* (2006.01)
*A61F 2/00* (2006.01)

(52) U.S. Cl.
USPC .......................... 424/426; 424/602

(58) Field of Classification Search
None
See application file for complete search history.

(56) References Cited

U.S. PATENT DOCUMENTS

| | | | |
|---|---|---|---|
| 4,157,437 A | 6/1979 | Okuzumi et al. |
| 4,178,686 A | 12/1979 | Riess et al. |
| 5,084,051 A | 1/1992 | Tormala et al. |
| 5,380,328 A | 1/1995 | Morgan |
| 5,387,377 A | 2/1995 | Chuang |
| 5,397,359 A | 3/1995 | Mittelmeier et al. |
| 5,639,402 A | 6/1997 | Barlow et al. |
| 5,700,559 A | 12/1997 | Sheu et al. |

(Continued)

FOREIGN PATENT DOCUMENTS

| | | |
|---|---|---|
| CN | 1363631 | 8/2002 |
| DE | 19721661 | 11/1998 |

(Continued)

OTHER PUBLICATIONS

Australian Patent Application No. 2005-254025: Examination Report dated Oct. 30, 2009, 2 pages.

(Continued)

*Primary Examiner* — Shanon A Foley
(74) *Attorney, Agent, or Firm* — Baker & Hostetler LLP (57) ABSTRACT

The present invention relates in general to implantable flexible bone composites, and method for preparing the same. The flexible bone composite includes at least one polymeric layer and at least one calcium-containing layer. The polymeric layer can be a polymeric layer including a synthetic polymer. The calcium-containing layer can include a calcium compound such as $\beta\text{-}Ca_3(PO_4)_2$. The flexible bone composites of the invention are useful as bone void fillers and have improved handling characteristics.

20 Claims, 2 Drawing Sheets (56) References Cited

U.S. PATENT DOCUMENTS

| | | | |
|---|---|---|---|
| 5,716,413 A * | 2/1998 | Walter et al. | 424/423 |
| 5,766,618 A | 6/1998 | Laurencin et al. | |
| 5,807,636 A | 9/1998 | Sheu et al. | |
| 5,824,088 A | 10/1998 | Kirsch | |
| 5,837,377 A | 11/1998 | Sheu et al. | |
| 5,919,234 A | 7/1999 | Lemperle et al. | |
| 5,968,253 A | 10/1999 | Poser et al. | |
| 6,096,855 A | 8/2000 | Sodergard et al. | |
| 6,350,284 B1 | 2/2002 | Tormala et al. | |
| 6,383,190 B1 | 5/2002 | Preissman | |
| 6,530,958 B1 * | 3/2003 | Cima et al. | 623/23.51 |
| 6,811,776 B2 | 11/2004 | Kale et al. | |
| 6,905,516 B1 * | 6/2005 | Lemaitre et al. | 623/23.56 |
| 7,056,968 B2 | 6/2006 | Hiraide et al. | |
| 8,012,501 B2 * | 9/2011 | Kerr et al. | 424/426 |
| 8,221,782 B2 * | 7/2012 | Kerr et al. | 424/426 |
| 2003/0180376 A1 | 9/2003 | Dalal et al. | |
| 2005/0216008 A1 * | 9/2005 | Zwirnmann et al. | 606/69 |

FOREIGN PATENT DOCUMENTS

| | | |
|---|---|---|
| EP | 19721661 | 11/1998 |
| JP | 01/501289 | 5/1989 |
| JP | 02/241460 | 9/1990 |
| JP | 03/085179 | 4/1991 |
| JP | 04/221538 | 8/1992 |
| JP | 07/313583 | 12/1995 |
| JP | 07/313586 | 12/1995 |
| JP | 08/024347 | 1/1996 |
| JP | 09/201330 | 8/1997 |
| JP | 09/512185 | 12/1997 |
| JP | 2000/126280 | 5/2000 |
| JP | 2003/210570 | 7/2003 |
| WO | WO 97/36553 | 10/1997 |
| WO | WO 01/32100 | 5/2001 |
| WO | WO 03/009878 | 2/2003 |
| WO | WO 2004/032988 | 4/2004 |
| WO | WO 2005/000483 | 1/2005 |
| WO | WO 2005/123155 | 12/2005 |

OTHER PUBLICATIONS

Chinese Patent Application No. 200580027197.7: Office Action dated Oct. 16, 2009, 3 pages.
Chinese Patent Application No. 200580027197.7: Response dated Aug. 11, 2009, 12 pages.
European Patent Application No. 04750971.6: Communication dated Jun. 12, 2008, 5 pages.
European Patent Application No. 05760224.5: Communication dated Apr. 2, 2007, 6 pages.
European Patent Application No. 05760224.5: Communication dated May 20, 2011.
European Patent Application No. 05760224.5: Response dated Oct. 12, 2007, 18 pages.
International Patent Application No. PCT/US2005/020484: International Search Report dated Dec. 12, 2005, 4 pages.
International Patent Application No. PCT/US2005/020484: Written Opinion dated Dec. 12, 2005, 8 pages.
Japanese Patent Application No. 2002-506661: Office Action dated Feb. 27, 2008, 7 pages.
Japanese Patent Application No. 2002-506661: Office Action dated Jul. 11, 2008, 4 pages.
Japanese Patent Application No. 2011-127249: Office Action dated May 7, 2013, 6 pages.
Kaneko et al., "Synthesis and Swelling—Deswelling Kinetics of Poly(N-Isopropylacrylamide) Hydrogels Grafted with LCST Modulated Polymers", J. Biomaterials Science, Polymer Edition, 1999, 10(11), 1079-1091.
Korean Patent Application No. 2006-7026310: Final Office Action dated Nov. 2, 2009, 3 pages.
Korean Patent Application No. 2006-7026310: Office Action dated May 29, 2009, 3 pages.
Liu et al., "Covalent Bonding of PMMA, PBMA and Poly(HEMA) to Hydroxyapatite Particles", J of Biomedical Materials Research, 1998 40, 257-263.
New Zealand Patent Application No. 552026: First Examiner Report dated Apr. 22, 2009, 2 pages.
Stile et al., "Synthesis and Characterization of Injectable Poly(N-Isopropylacrylamide)—Based Hydrogels That Support Tissue Formation in Vitro", Macromolecules, 1999, 32, 7370-7379.

* cited by examiner

FLEXIBLE BONE COMPOSITE

CROSS REFERENCE TO RELATED APPLICATIONS

This application is a continuation of U.S. patent application Ser. No. 13/539,779 filed on Jul. 2, 2012, which is a continuation of U.S. patent application Ser. No. 13/208,837 filed on Aug. 12, 2011, now U.S. Pat. No. 8,221,782, which is a continuation of U.S. patent application Ser. No. 11/148,193 filed on Jun. 9, 2005, now U.S. Pat. No. 8,012,501, which claims the benefit of prior U.S. provisional application Ser. No. 60/578,610 filed on Jun. 10, 2004, each of which is incorporated herein by reference in its entirety.

FIELD OF THE INVENTION

The present invention includes flexible bone composites including at least one polymeric layer and at least one calcium-containing layer, and methods for making the same. The composites of the invention have improved handling characteristics.

BACKGROUND OF THE INVENTION

An area of interest with regard to bone cements or calcium phosphate compositions focuses on reinforcing bone cements with various materials. Often ceramic bone cements, though strong, are brittle and not sufficiently resistant to catastrophic failure (e.g., through cracking) to function as a matrix material. Polymers can be used to reinforce ceramic bone components. For example, implantable composite materials containing a strong and resilient matrix impregnated with reinforcing filler particles, whiskers, or meshes are known. Resorbable implant materials, such as polylactides and polyglycolides, compared to traditional, non-resorbable metal or composite materials, for example, have the advantage of being biocompatible, of being biodegradable after a period of time, and of not requiring removal, e.g., in bone fixation or repair applications. These qualities can be useful for implant matrices that are designed to be temporary place fillers (and in some cases, stabilizing components) for healing and/or regrowth, e.g., of bone voids or defects.

SUMMARY OF THE INVENTION

The present invention includes flexible bone composites including at least one polymeric layer and at least one calcium-containing layer.

In one embodiment, the flexible bone composite includes: (a) a polymeric layer having a first side and a second side; and (b) a first calcium-containing layer affixed or physically and/or chemically attached to the first side of the polymeric layer.

In another embodiment, the flexible bone composite includes: (a) a perforated polymeric layer having a first side and a second side; and (b) a calcium-containing layer affixed or physically and/or chemically attached to the first side of the polymeric layer.

The invention also includes methods for making a flexible bone composite including at least one polymeric layer and at least one calcium-containing layer.

In one embodiment, the invention includes a method for making a flexible bone composite including a polymeric layer having a first side and a second side, including: disposing a calcium compound onto the first side of the polymeric layer to form a first calcium-containing layer.

In another embodiment, the invention includes a method for making a flexible bone composite including a polymeric layer having a first side and a second side, including: contacting a first calcium compound with the first side of the polymeric layer to form a first intermediate composite; and heating the first intermediate composite at a temperature sufficient to affix or to physically and/or chemically attach the first calcium compound to the first side of the polymeric layer and provide a first calcium-containing layer.

In another embodiment, the invention includes a method for making a flexible bone composite including a polymeric layer having a first side and a second side, including: casting a solution including the polymer and a solvent onto a release surface; allowing the solution to gel; contacting a calcium compound with a first side of the gel; and allowing the solvent to evaporate from the gel to form a flexible bone composite having a first calcium-containing layer affixed or physically and/or chemically attached to the first side of the polymeric layer.

In another embodiment, the invention includes a method for making a flexible bone composite including a perforated polymeric layer having a first side and a second side, including: perforating a polymeric layer to form a perforated polymeric layer; heating the perforated polymeric layer; contacting a first calcium compound with the first side of the perforated polymeric film to form a first intermediate composite; and allowing the first intermediate composite to cool to a temperature sufficient to affix or to physically and/or chemically attach the first calcium compound to the first side of the perforated polymeric layer and provide a calcium-containing layer.

In another embodiment, the invention includes methods for treating a hard tissue defect in a patient in need thereof.

In another embodiment, the invention includes a method for treating a bone defect in a patient in need thereof, including: implanting a therapeutically effective amount of a flexible bone composite including at least one polymeric layer and at least one calcium-containing layer into the defect.

In another embodiment, the present invention includes a flexible bone cement composition that can be molded to fill voids such as, e.g., bone voids, and a method for making such composition. In another embodiment, the invention includes a flexible calcium-containing composite material for implantation that exhibits improvements in key mechanical properties as a result of a specific combination of properties of the ingredients.

In another embodiment, the present invention also includes kits including a container which contains a flexible bone composite including at least one polymeric layer and at least one calcium-containing layer.

The details of the invention are set forth in the accompanying description and examples below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise.

DETAILED DESCRIPTION OF THE PREFERRED EMBODIMENTS

As noted above, the present invention includes a flexible bone composite including at least one polymeric layer and at least one calcium-containing layer. Generally, the at least one polymeric layer has a first side and a second side and the at least one calcium-containing layer is disposed at least on the first side of the at least one polymeric layer.

The polymeric layer includes a polymer. The polymer can be a resorbable polymer, a non-resorbable polymer, or a combination thereof. In one embodiment, the polymeric layer contains less than about 10% by weight of non-resorbable polymer, preferably less than about 5% by weight of non-resorbable polymer, more preferably less than about 1% by weight of non-resorbable polymer, based on the total weight of the polymeric layer.

In a preferred embodiment, the polymeric layer includes a resorbable polymer, and the polymeric layer is substantially free of a non-resorbable polymer. Preferably, the resorbable polymeric layer is resorbable in vivo and includes a resorbable polymer.

The polymer in the polymeric layer can include a synthetic polymer, a non-synthetic polymer (i.e., a polymer obtained from a plant or animal), or a combination thereof. In one embodiment, the polymeric layer includes a synthetic polymer, and the polymeric layer is substantially free of non-synthetic polymer. For example, the polymeric layer may contain less than about 10% by weight of non-synthetic polymer, preferably less than about 5% by weight of non-synthetic polymer, more preferably less than about 1% by weight of non-synthetic polymer, based on the total weight of the polymeric layer.

In one embodiment, the flexible bone composite includes a polymeric layer including a synthetic polymer and a calcium-containing layer.

In another embodiment, the flexible bone composite includes: (a) a polymeric layer including a synthetic polymer, wherein the polymeric layer is substantially free of non-synthetic polymer; and (b) a calcium-containing layer. As used herein, the phrase "substantially free" should be understood to mean that less than about 0.5% by weight of the substantially free component is present, preferably less than about 0.2% by weight, more preferably less than about 0.1% by weight, and often none.

In another embodiment, the flexible bone composite includes: (a) a polymeric layer including a synthetic polymer, wherein the polymeric layer is substantially free of non-synthetic polymer and substantially free of non-resorbable polymer; and (b) a calcium-containing layer.

In one embodiment, the flexible bone composite includes: (a) a polymeric layer including a synthetic resorbable polymer and having a first side and a second side; and (b) a first calcium-containing layer affixed or chemically and/or physically attached to the first side of the polymeric layer.

In another embodiment, the flexible bone composite includes: (a) more than one polymeric layer, at least a first polymeric layer, preferably an exterior layer, including a synthetic non-resorbable polymer and having a first side and a second side, wherein the first polymeric layer is substantially free of resorbable polymer, and at least a second polymeric layer, preferably an interior layer, including a resorbable polymer and having a first side and a second side; and (b) a first calcium-containing layer affixed or chemically and/or physically attached at least to the first side of the first polymeric layer and at least to the first side of the second polymeric layer.

As used herein, the term "polymer" includes homopolymers and copolymers (i.e., polymers including two or more different monomeric units). As used herein, the generic term "copolymer" includes, but is not limited to, alternating copolymers, random copolymers, block copolymers, or any combination thereof.

In one embodiment, the polymeric layer contains less than about 25% by weight of calcium-containing compound based on the total weight of the polymeric layer. In another embodiment, the polymeric layer contains less than about 10% by weight of calcium-containing compound based on the total weight of the polymeric layer. In another embodiment, the polymeric layer contains less than about 1% by weight of calcium-containing compound based on the total weight of the polymeric layer. Preferably, the polymeric layer is substantially free of calcium compounds.

Examples of polymers useful for preparing the polymeric layer include, but are not limited to, homopolymers or copolymers of monomers selected from L-lactide; L-lactic acid; D-lactide; D-lactic acid; glycolide; α-hydroxybutyric acid; α-hydroxyvaleric acid; α-hydroxyacetic acid; α-hydroxycaproic acid; α-hydroxyheptanoic acid; α-hydroxydecanoic acid; α-hydroxymyristic acid; α-hydroxyoctanoic acid; α-hydroxystearic acid; hydroxybutyrate; hydroxyvalerate; β-propiolactide; β-propiolactic acid; γ-caprolactone; β-caprolactone; ε-caprolactone; γ-butyrolactone; pivalolactone; tetramethylglycolide; tetramethylglycolic acid; dimethylglycolic acid; trimethylene carbonate; dioxanone; those monomers that form liquid crystal polymers; those monomers that form cellulose; those monomers that form cellulose acetate; those monomers that form carboxymethylcellulose; those monomers that form hydroxypropylmethyl-cellulose; polyurethane precursors including macrodiols selected from polycaprolactone, poly(ethylene oxide), poly(ethylene glycol), poly(ethylene adipate), poly(butylene oxide), and a mixture thereof, isocyanate-functional compounds selected from hexamethylene diisocyanate, isophorone diisocyanate, cyclohexane diisocyanate, hydrogenated methylene diphenylene diisocyanate, and a mixture thereof, and chain extenders selected from ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof, and any combination of two or more of the foregoing.

In one embodiment, the polymeric layer includes resorbable polymers. Non-limiting examples of resorbable polymers include, e.g., polymers derived from monomers selected from L-lactic acid, D-lactic acid, L-lactide, D-lactide, D,L-lactide, glycolide, a lactone, a lactam, ε-caprolactone, trimethylene carbonate, a cyclic carbonate, a cyclic ether, para-dioxanone, beta-hydroxybutyric acid, beta-hydroxypropionic acid, beta-hydroxyvaleric acid, saccharides, collagen, fibrin, albumin; and any combination of two or more of the foregoing.

In another embodiment, the polymeric layer includes a resorbable synthetic polymer. Non-limiting examples of resorbable synthetic polymers include, e.g., a poly(L-lactide) (co)polymer, a poly(D,L-lactide) (co)polymer, a polyglycolide (co)polymer, a polycaprolactone (co)polymer, a poly(tetramethylglycolic acid) (co)polymer, a polydioxanone (co)polymer, a polyhydroxybutyrate (co)polymer, a polyhydroxyvalerate (co)polymer, a poly(L-lactide-co-glycolide) copolymer, a poly(glycolide-co-trimethylene carbonate) copolymer, a poly(glycolide-co-caprolactone) copolymer, a poly(glycolide-co-dioxanone-co-trimethylene carbonate) copolymer, a poly(tetramethylglycolic acid-co-dioxanone-co-trimethylene carbonate) copolymer, a poly(glycolide-co-caprolactone-co-L-lactide-co-trimethylene carbonate) copolymer, a poly(lactide-co-caprolactone) copolymer, a poly(hydroxybutyrate-co-hydroxyvalerate) copolymer, a liquid crystal (co)polymer, a combination thereof, or a copolymer thereof.

In one embodiment, the polymeric layer includes a poly(L-lactide-co-glycolide) copolymer.

In another embodiment, the polymeric layer includes monomers selected from L-lactide; D-lactide, D,L-lactide, ε-caprolactone, trimethylene carbonate; para-dioxanone, and any combination of two or more of the foregoing.

In another embodiment, the polymeric layer includes a copolymer of L-lactide and ε-caprolactone.

In another embodiment, the polymeric layer includes a copolymer of 70% L-lactide and 30% ε-caprolactone (e.g., 70:30 poly(L-lactide-co-ε-caprolactone)).

In one embodiment, the poly(L-lactide-co-glycolide) copolymer includes at least about 15% of glycolide repeat units and at least about 15% of L-lactic acid repeat units. In another embodiment, the poly(L-lactide-co-glycolide) copolymer includes about 82% of glycolide repeat units and about 18% of L-lactic acid repeat units. In another embodiment, the poly(L-lactide-co-glycolide) copolymer includes about 18% of glycolide repeat units and about 82% of L-lactic acid repeat units.

In another embodiment, the polymeric layer includes a non-resorbable polymer. Non-limiting examples of non-resorbable polymers include, e.g., polyethylene, polypropylene, and polyurethanes.

The polymeric layers are commercially available or can be made by polymerizing the various types of monomers (e.g., L-lactide, glycolide) using any suitable method such as those described below. When the polymeric layers includes two or more different monomers, i.e., a copolymer, any method capable of forming the copolymer such that the biodegradation or resorbability and the mechanical properties (e.g., before and during implantation) are sufficient for the requirements of the application for which the copolymer is to be used. For example, one such polymerization method can be found in U.S. Pat. No. 6,096,855, the entire disclosure of which is incorporated herein by reference hereto. Other examples of copolymerization methods for producing poly(D,L-lactide-co-glycolide) and other random copolymers are disclosed in U.S. Pat. No. 4,157,437 and International Publication No. WO 97/36553, the entire disclosures of which are also incorporated herein by reference hereto.

Advantageously, in one embodiment, the polymers from which the polymeric layer is formed must have a sufficient molecular weight to be able to perform (e.g., mechanically) in the desired application. Generally, a sufficiently high molecular weight can be obtained by polymerizing substantially all (i.e., preferably at least about 98 mol %, more preferably at least about 99 mol %, most preferably at least about 99.5 mol %) of the monomeric and/or dimeric copolymer substituents. As used herein, the term "molecular weight" should be understood to mean extent of polymerization, or number or weight average of monomeric or dimeric units in the copolymer chains. Molecular weight, as used herein, can be approximated by a number of known methods, e.g., such as by gel permeation or size exclusion chromatography (GPC or SEC), by inherent or intrinsic viscosity analysis (I.V.), or by an equivalent scientific technique through which a correlation can be made to estimate copolymer molecular weight.

When measured by GPC or SEC against polystyrene standards, the polymers according to the invention (before being processed or fabricated into films) can, in one embodiment, exhibit a number average molecular weight of at least about 75,000 grams/mole, for example from about 150,000 grams/mole to about 1,000,000 grams/mole or from about 250,000 grams/mole to about 900,000 grams/mole. Such measurements can, in another embodiment, also yield a weight average molecular weight of at least about 125,000 grams/mole, for example at least about 250,000 grams/mole or from about 400,000 grams/mole to about 2,500,000 grams/mole. Alternately, in some embodiments, the number average molecular weight can be between about 16,000 grams/mole and about 75,000 grams/mole or between about 18,000 grams/mole and about 50,000 grams/mole, and the number average molecular weight can be between about 50,000 grams/mole and about 150,000 grams/mole or between about 60,000 grams/mole and about 120,000 grams/mole.

In another embodiment, such measurements can also show a polydispersity (i.e., a ratio of weight average molecular weight to number average molecular weight) from about 1.3 to about 3.5, for example from about 1.6 to about 2.8 or from about 1.85 to about 2.5. The desired application for which the polymeric layers will be used should generally determine the acceptable range of molecular weight values, e.g., a copolymer used for drug delivery, maxillofacial implant, or other application in which enhanced biodegradation or resorbability is paramount, may be preferred to exhibit number average and/or weight average molecular weights in a lower region of, or even below, the ranges listed above, whereas a copolymer used in a pin, rod, anchor, staple, or other mechanically-intensive and/or load-bearing application may be preferred to exhibit number average and/or weight average molecular weights in an intermediate or upper region of, or even above, the ranges listed above.

When measured for I.V. at a concentration of about 0.1% w/v in chloroform, the polymers according to the invention (before being processed or fabricated into layers) can, in one embodiment, exhibit an inherent viscosity of at least about 1.0 dl/g, for example from about 2.5 dug to about 8 dl/g, from about 3 dug to about 7 dl/g or from about 4 Wig to about 6.5 dl/g. In another embodiment, the inherent viscosity of the poly(L-lactide-co-glycolide) copolymer of the invention can be greater than about 4.5 dl/g. The desired application for which the polymers will be used should generally determine the acceptable range of inherent viscosity values, e.g., a copolymer used for drug delivery, maxillofacial implant, or other application in which enhanced biodegradation or resorbability is paramount, may be preferred to exhibit lower inherent or intrinsic viscosities than those listed above, whereas films used in a composite for a pin, rod, anchor, staple, or other mechanically-intensive and/or load-bearing application may be preferred to exhibit inherent or intrinsic viscosities within, or even above, those listed above.

The polymers can have a low moisture (or water) content (i.e., before being combined with the calcium compound-containing component), for example, not more than about 1.5% by weight or not more than about 1% by weight. In one embodiment, the moisture or water content can be not more than about 500 ppm, for example not more than about 250 ppm or not more than about 150 ppm. In other embodiments, the moisture or water content of polymers according to the invention can be not more than about 200 ppm or not more than about 100 ppm.

In some embodiments, the polymers can be subject to a drying and/or volatile organic compound (VOC) removal step, in order to remove water, organic solvent(s), unreacted monomer/dimer, or other low molecular weight and/or volatile impurities or compounds that can be present in the polymers. This drying/removal step can include, but is not limited to, introduction of a relatively-dry, inert gas (e.g., such as dry nitrogen, argon, or the like, or a mixture containing such a gas), application of a vacuum (e.g., such that the pressure is not more than about 10 Torr, for example more than about 5 Ton or not more than about 1 Ton:), application of an increased temperature (e.g., of at least about 50° C., for example at least about 65° C. such as from about 70° C. to about 120° C., and also preferably, provided that the copolymer is at least partially crystalline, that the increased temperature is not greater than about 5° C. below its melting temperature, for example not greater than about 10° C. below its melting temperature), or any combination thereof. This drying/removal step is generally undertaken for a period of time sufficient to render the moisture content within acceptable or preferred limits. When performed, the step can advantageously include a combination of application of increased temperature and application of a vacuum and occurs for at least about 4 hours, for example for at least about 12 hours, or alternately for not more than about 24 hours or from about 16 hours to about 20 hours.

The polymers can exhibit a wide range of degrees of crystallinity, with preferable values depending upon the desired application for which they are to be used. In one embodiment, the polymeric layers are semicrystalline and can exhibit a degree of crystallinity from about 15% to about 30%, for example from about 20% to about 30%, or for example from about 20% to about 26%. In another embodiment, the layers of the invention can exhibit a degree of crystallinity of less than about 15%. In an alternate embodiment, the layers of the invention can exhibit a degree of crystallinity from about 15% to about 50%. In other alternate embodiments, the layers of the invention can exhibit a degree of crystallinity of less than about 10%, less than about 5%, less than about 1%, or can exhibit substantially no crystallinity (i.e., less than about 0.5%, preferably less than about 0.1%, or at any rate not quantitatively detectable by one or more experimental methods). The "degree of crystallinity" can be measured by a number of well-known experimental techniques and, when the term is used herein, reflects the relative proportion, by volume, cross-sectional area, or linear path through a sample, of crystalline regions in comparison to non-crystalline or amorphous regions of the films. Suitable experimental techniques to measure degree of crystallinity include, but are not limited to, differential scanning calorimetry (DSC), x-ray scattering or diffraction methods (e.g., XRD, WARD, WARS, etc.), or the like.

The polymers may also exhibit a wide range of degrees of crystalline perfection (or crystalline imperfection), again with preferable values depending upon the desired application for which they are to be used. The degree of crystalline perfection or imperfection can be measured, for example, by DSC or another well-known experimental technique and can be referred to herein in terms of a heat of fusion ($\Delta H_f$), which represents the relative perfection or imperfection of the crystals of the copolymer in terms of the amount of energy per unit of material (e.g., in Joules per gram, J/g, or milliJoules per milligram, mJ/mg) required to melt, or de-crystallize, the crystals of the copolymer. In one embodiment, the films of the invention are semicrystalline and can exhibit a heat of fusion of less than about 50 J/g, for example less than about 30 J/g or less than about 25 J/g. In another embodiment, the films of the invention can exhibit a heat of fusion from about 50 J/g to about 70 J/g. In alternate embodiments, the films of the invention can exhibit a heat of fusion of from about 0.5 J/g to about 15 J/g, from about 0.1 J/g to about 10 J/g, from about 15 J/g to about 25 J/g, or can exhibit substantially no heat of fusion (i.e., less than about 0.1 J/g, or at any rate not quantitatively detectable by one or more experimental methods).

Melting temperatures and glass transition temperatures for the polymers can also vary, with preferable values depending upon the desired application for which they are to be used. Melting and glass transition temperatures can be measured, for example, by DSC or another well-known experimental technique, and are generally dependent upon the rate at which temperature is increased or decreased. Standard DSC tests are performed with temperature changing at a rate of about 5° C./min to about 20° C./min, particularly at about 10° C./min. The melting temperature of the polymeric layers of the present invention, as measured by standard DSC tests, can, in one embodiment, be between about 90° C. and about 225° C., for example from about 110° C. to about 165° C. or from about 130° C. to about 150° C. The glass transition temperatures of the polymers, as measured by standard DSC tests, can, in another embodiment, be between about 30° C. and about 100° C., for example between about 40° C. and about 60° C.

Values for various mechanical properties of the polymers can vary widely, depending inter alfa upon the desired application for which they are to be used and the process by which they are formed into articles or devices for said applications. For example, in one embodiment, the tensile strength of the polymers can range from about 10 to about 100 MPa. In another embodiment, the elastic modulus of the polymers can range from about 0.1 to about 6 GPa.

As the polymers and/or compositions have utility in implantations and in vivo applications, it may be desirable to sterilize such polymers and/or composites to minimize in vivo response, e.g., from infection, foreign body rejection, or the like. Because the resorbable polymers of the invention are resorbable or degradable in the presence of water, sterilization methods other than autoclaving are particularly appropriate. Such sterilization processes can include, but are not limited to, exposure to ethylene oxide, exposure to γ-radiation, exposure to an electron beam source, exposure to a cold (or at least low-temperature) plasma source, or a combination thereof. The sterilization process, depending upon the exposure dose and duration, is one possible way to introduce branching, grafting, or crosslinking to the polymers.

In one embodiment, single or multiple doses to these means of sterilization can be performed on the polymers, articles, or devices according to the invention in an amount, or in amounts, sufficient to prevent, inhibit, or curtail in vivo response. In one preferred embodiment, the sterilization includes a single dose exposure to radiation or ethylene oxide. In another preferred embodiment, the sterilization includes a single dose exposure of the poly(L-lactide-co-ε-caprolactone) copolymers or composites according to the invention to γ-radiation of about 25 kGy.

When the resorbable polymeric layer includes resorbable polymers, the flexible bone composites containing them tend to exhibit complete in vivo or in vitro resorption from about 1 month to about 2.5 years, for example from about 2 months to about 2 years. As used herein, "complete resorption" refers to the situation where, upon visual inspection, there is either no evidence of polymeric material at the site of implantation, or where, upon analysis of a sample of the implantation site of the degraded polymer, there is an absence of oligomeric material resultant from degradation of the polymer that has a number average molecular weight of more than about 1,000 grams/mole or not more than about 500 grams/mole. In another embodiment, the polymers and/or compositions according to the invention should typically retain at least a portion of their mechanical properties after implantation in vivo or after exposure to a phosphate buffered saline (PBS) solution having a pH of about 7.4 (±0.2) at a temperature of about 37° C. (±1° C.).

The polymeric layer can be prepared by methods known in the art. For example, in one embodiment, the polymeric layer can prepared using conventional viscoelastic-liquid forming or liquid-setting means including, but not limited to, extrusion, compression molding, injection molding, thermoforming, blow molding, rotational molding, calendaring and casting (see, e.g., Joel R. Fried, *Polymer Science and Technology*, pages 373-384 (1995), and K. J. Mackenzie, "Film and Sheeting Materials" in 10 *Kirk Othmer: Encyclopedia of Chemical Technology* 775-787 (1993), the entire contents of each of the foregoing references being incorporated herein by reference).

For example, in another embodiment, the polymeric layer can be prepared by compression molding or calendaring.

In one embodiment, the polymeric layer is in the form of a film.

The amount and thickness of the polymeric layer can vary. In general, the polymeric layer is present in an amount sufficient to provide a flexible platform for the calcium-containing layer(s). In one embodiment, the polymeric layer is present in an amount ranging from about 1% by weight to about 99% by weight based on the total amount of the flexible bone composite. In another embodiment, the polymeric layer is present in an amount ranging from about 10% by weight to about 75% by weight based on the total amount of the flexible bone composite. In another embodiment, the polymeric layer is present in an amount ranging from about 25% by weight to about 30% by weight based on the total amount of the flexible bone composite.

The polymeric layer(s) may be of any suitable thickness (es). For example, the polymeric layer can have a thickness ranging from about 0.01 mm to about 1.0 mm. In one embodiment, the polymeric layer has a thickness ranging from about 0.05 mm to about 0.5 mm. In another embodiment, the polymeric layer has a thickness ranging from about 0.05 mm to about 0.25 mm. In a preferred embodiment, the polymeric layer has a thickness ranging from about 0.05 mm to about 0.15 mm.

In one embodiment, the polymeric layer may be perforated with one or more perforations. Such perforations may provide pathways for liquids to penetrate the polymeric layer. The perforations may be of any size and shape and distributed in any pattern. For example, in some embodiments, the perforations can be distributed homogeneously over the polymeric layer. When the polymeric layer is perforated, in one embodiment, the extent of perforation can range from about 1% to about 90% by area based on the total surface area of the first or second side of the polymeric layer; in another embodiment, the extent of perforation can range from about 5% to about 75% by area based on the total surface area of the first or second side of the polymeric layer; and in another embodiment, the extent of perforation can range from about 15% to about 50% by area based on the total surface area of the first or second layer of the polymeric layer. In a preferred embodiment, the extent of perforation is about 22% by area based on the total surface area of the first or second layer of the polymeric layer.

Methods for perforating the polymeric layer include, but are not limited to, punching holes through the polymeric layer using a punch, a die, a calendering roller, or slitting the polymeric layer with a knife or scalpel.

The diameter of the holes in the perforated layer can vary or can be within a predetermined tolerance. In one embodiment, the diameter of the holes ranges from about 0.4 mm to about 6.5 mm; in another embodiment, the diameter of the holes ranges from about 0.8 mm to about 3.5 mm; and in another embodiment, the diameter of the holes ranges from about 1.0 mm to about 2 mm. In a preferred embodiment, the diameter of the holes is about 1.5 mm.

In certain embodiments, where the polymeric layer is perforated by slicing the film with a knife or scalpel, the length of the cuts or slits can vary. In one embodiment, the length of the cut ranges from about 0.5 to about 10 mm; in another embodiment, the length of the cut ranges from about 1 to about 5 mm; and in another embodiment, the length of the cut ranges from about 2 to about 3 mm.

In one embodiment, the invention includes a flexible bone composite including: (a) a perforated polymeric layer having a first side and a second side; and (b) a first calcium-containing layer affixed or physically and/or chemically attached to the first side of the polymeric layer. In another embodiment, the invention includes a flexible bone composite including: (a) a perforated resorbable polymeric layer having a first side and a second side; and (b) a first calcium-containing layer affixed or physically and/or chemically attached to the first side of the resorbable polymeric layer.

In another embodiment, the flexible bone composite includes a second resorbable polymeric layer. In another embodiment, the second polymeric layer can be affixed or physically and/or chemically attached to the second side of the polymeric layer or the first calcium-containing layer. Non-limiting examples of polymeric layers useful for making the second polymeric layer include homopolymers or copolymers discussed above for the polymeric layer.

In one embodiment, the second polymeric layer is resorbable and includes a synthetic polymer.

In another embodiment, the second polymeric layer is perforated, as described above for the polymeric layer.

In yet another embodiment, the second resorbable polymeric layer is not perforated.

The thickness of the second polymeric layer can be any suitable thickness, as described above for the polymeric layer. In one embodiment, the polymeric layer and the second polymeric layer have the same thickness. In another embodiment, the thickness of the polymeric layer and the second polymeric are different.

As noted above, the flexible bone composite includes a first calcium-containing layer including a calcium compound. The calcium-containing layer can be affixed or physically and/or chemically attached to at least one side, such as the first side, of the polymeric layer. Methods of affixing or physically and/or chemically attaching the calcium-containing layer on the polymeric layer are described below.

The calcium compounds can be porous or non-porous. The term "porous" includes, but is not limited to, macroporosity (mean pore diameter greater than or equal to 100 microns), mesoporosity (mean pore diameter less than 100 microns but greater than or equal to 10 microns) and microporosity (mean pore diameter less than 10 microns).

The pores may be of any size, shape or distribution, or within a predetermined tolerance. In addition, the pores can be interconnecting or non-interconnecting. In one embodiment, the diameter of the pores can range in size up to about 750 microns. In another embodiment, the calcium compound is porous with pore sizes ranging up to about 500 microns, with approximately 75% of the pores being at least 100 microns in size and the remaining 25% of the pores being no more than 10 microns in size.

In cases where the calcium compound is affixed or physically and/or chemically attached to the polymeric layer, a majority of the external surface of the calcium compound is not covered with polymer. The limited external coverage of the calcium compounds may provide for enhanced resorption.

In one embodiment, the calcium-containing layer contains less than about 25% by weight of polymer based on the total weight of the calcium-containing layer. In another embodiment, the calcium-containing layer contains less than about 10% by weight of polymer based on the total weight of the calcium-containing layer. In another embodiment, the calcium-containing layer contains less than about 1% by weight of polymer based on the total weight of the calcium-containing layer. Preferably, the calcium-containing layer is substantially free of polymer.

In one embodiment, the calcium compounds have less than about 5% by weight, preferably less than 1% by weight, more preferably less than 0.5% by weight, of hydroxyapatite based on the total weight of the calcium compound. In another embodiment, the calcium compound is substantially free of hydroxyapatite.

In another embodiment, the calcium-containing layer can include any calcium bone cement. Non-limiting examples of useful calcium compounds include calcium phosphates, calcium sulfates, calcium carbonates, or any combination thereof. Preferably, the calcium compound is a calcium salt.

In one embodiment, the first calcium-containing layer includes a calcium phosphate. Non-limiting examples of calcium phosphates includes amorphous calcium phosphate, crystalline calcium phosphate, or any combination thereof.

In another embodiment, the first calcium-containing layer includes calcium phosphate, wherein the calcium phosphate is $CaHPO_4 \cdot nH_2O$, $\alpha\text{-}Ca_3(PO_4)_2$, $\alpha\text{-bar-}Ca_3(PO_4)_2$, $\beta\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $Ca_2P_2O_7$, $Ca(H_2PO_4)_2 \cdot nH_2O$, $Ca_8H_2(PO_4)_6 \cdot nH_2O$, or any combination thereof, where n is a number ranging from 0 to 5.

In another embodiment, the first calcium-containing layer includes $\beta\text{-}Ca_3(PO_4)_2$.

In another embodiment, the first calcium-containing layer includes $\beta\text{-}Ca_3(PO_4)_2$, wherein the $\beta\text{-}Ca_3(PO_4)_2$ is substantially free of hydroxyapatite.

In another embodiment, the first calcium-containing layer includes a calcium sulfate. The calcium sulfate can be amorphous or crystalline. Non-limiting examples of useful calcium sulfates include $Ca(SO_4)$, $\alpha\text{-}Ca(SO_4) \cdot \frac{1}{2}H_2O$, $\beta\text{-}Ca(SO_4) \cdot \frac{1}{2}H_2O$, or any combination thereof.

The calcium compounds used in the present invention can be of any shape including, for example, spherical, cubic, wedge-shaped, oblong, cylindrical, or combinations thereof. In one embodiment, the calcium compounds are spherical. In another embodiment, the calcium compounds are cubic.

The calcium compounds may be particles or granules of any size or shape. The granules are available commercially or can be obtained by grinding or milling a calcium compound to a desired particle size or particle diameter. The granules can be classified by, for example, sieving, to obtain the desired range of particle diameters (see *Perry's Chemical Engineering Handbook*, chapter 21, pages 13-19 (Don. W. Green ed. 1984)).

In one embodiment, the mean diameter of the granules range in size from about 0.05 mm to about 10 mm. In another embodiment, the mean diameter of the granules range in size from about 0.075 mm to about 5 mm. In another embodiment, the mean diameter of the granules range in size from about 0.075 mm to about 1 mm. In another embodiment, the mean diameter of the granules range in size from about 1.4 mm to about 2.8 mm. In another embodiment, the mean diameter of the granules range in size from about 2.8 mm to about 5.6 mm. In another embodiment, the mean diameter of the granules range in size from about 0.1 mm to about 0.750 mm The specific surface area of the calcium compounds can vary. For example, when the calcium compound is a granule, the specific surface area can range from about 0.1 $m^2/g$ to about 100 $m^2/g$.

The amount and the thickness of the first calcium-containing layer can vary. In general, the amount of first calcium compound affixed or physically and/or chemically attached to the first side of the polymeric layer is an amount sufficient to provide the desired therapeutic effect while still maintaining the desirable properties of the composition, e.g., flexibility and resistance to delamination.

In one embodiment, an amount of the calcium compound ranges from about 1% to about 99% by weight based on the total weight of the flexible bone composite (i.e., the polymeric layer and the first calcium-containing layer); in another embodiment, an amount of the calcium compound ranges from about 5% to about 95% by weight based on the total weight of the flexible bone composite; and in another embodiment, the amount of the calcium compound ranges from about 70% to about 85% by weight based on the total weight of the flexible bone composite.

In one embodiment, the first calcium-containing layer has a thickness ranging from about 0.05 mm to about 10 mm. In another embodiment, first calcium-containing layer has a thickness ranging from about 0.075 mm to about 7.5 mm. In another embodiment, the first calcium-containing layer has a thickness ranging from about 2.8 mm to about 5.6 mm. In another embodiment, the first calcium-containing layer has a thickness ranging from about 1.4 mm to about 2.8 mm. In another embodiment, the first calcium-containing layer has a thickness ranging from about 0.1 mm to about 0.750 mm.

The density of calcium compound particles or granules disposed on or physically and/or chemically attached to the first side of the polymeric layer can vary. That is, the spacing between the calcium compound particles, may vary. For example, in one embodiment, a majority of the particles are within about 0.75 mm of at least one other calcium compound particle. In another embodiment, a majority of the particles are within about 0.25 mm of at least one other calcium compound particle. In another embodiment, a majority of the particles are within about 0.1 mm of at least one other calcium compound particle. In another embodiment, a majority of the particles are in contact with at least one other calcium compound particle.

Any suitable thickness of the first calcium-containing layer can be used. For example, a first calcium compound granule having diameter approximately equal to the desired thickness of the first calcium-containing layer is affixed or physically and/or chemically attached to a side of the polymeric layer as described below.

In addition, more than one calcium-containing layer may be used to form the flexible bone composite. For example, the flexible bone composite may include a second calcium-containing layer affixed or physically and/or chemically attached to the second side of the polymeric layer.

The second calcium-containing layer includes a second calcium compound. Non-limiting examples of useful second calcium compounds include those described above for the first calcium compounds. The second calcium compound can be the same as, or different than, the first calcium compound.

In one embodiment, the second calcium compound is substantially free of hydroxyapatite. In one embodiment, the second calcium compound is a calcium salt.

In another embodiment, the second calcium compound is calcium phosphate. In another embodiment, second calcium compound is $\beta$-$Ca_3(PO_4)_2$. In another embodiment, the second calcium compound is $\beta$-$Ca_3(PO_4)_2$, where the $\beta$-$Ca_3(PO_4)_2$ is substantially free of hydroxyapatite.

The thickness of the second calcium layer can be the same as, or different from, that of the first calcium-containing layer. In general, the thickness of the second calcium layer ranges from about 0.05 mm to about 10 mm.

The flexible composite can be formed into any thickness or shape before or after implantation.

In some embodiments, moreover, two or more flexible composites can be layered upon each other to provide a thicker composite with multiple polymeric layers and calcium-containing layers. For example, in one embodiment, the multi-layer flexible bone composite can include: (a) a first composite including: a first polymeric layer having a first side and a second side; and a first calcium-containing layer affixed or physically and/or chemically attached to the first side of the polymeric layer; and (b) a second composite including: a polymeric layer having a first side and a second side; and a second calcium-containing layer affixed or physically and/or chemically attached to the first side of the polymeric layer; wherein the first composite is affixed or physically and/or chemically attached to the second composite to form the multi-layer flexible bone composite that has alternating polymeric layers and calcium-containing layers. Additional composites may also be added to form the multilayer flexible bone composite. The composites used to make the multilayer flexible bone composite may be the same or different. In some multilayer embodiments, it may be advantageous for one or more of the exterior layers to contain non-resorbable polymers and for the one or more interior layers to contain predominantly resorbable polymers.

The multi-layer flexible bone composite can includes a porous calcium-containing component, a nonporous calcium-containing component, or a combination thereof. In one embodiment, the multi-layer flexible bone includes a porous calcium-containing component and a nonporous calcium-containing component. In another embodiment, the multi-layer flexible bone includes a porous calcium-containing component.

The multi-layer flexible bone composite can includes a resorbable polymeric layer, a non-resorbable polymeric layer, or a combination thereof. Preferably, the multi-layer flexible bone composite includes at least one resorbable polymeric layer including a synthetic polymer.

The plurality of composites may be affixed or chemically and/or physically attached to each other using any suitable methods. For example, in one embodiment, when two or more flexible composites are layered upon each, the resultant composite can optionally be heated. For instance, in some embodiments, the layered composites can be heated in a convection oven for a time and a temperature sufficient to make the polymeric layers tacky followed by cooling. In another embodiment, pressure is applied to the heated multi-layer composite.

In another embodiment, a flexible synthetic composite can be rolled up, e.g., like a jelly roll, to provide a thicker composite. In certain embodiments, it may be desirable for the portion of the rolled up composite that is on the exterior of the roll (e.g., on the outer circumference of the device shown in FIG. 6) to contain predominantly non-resorbable polymer and for the portion of the rolled up composite that is on the interior of the roll to contain predominantly resorbable polymer.

In some embodiments, the flexible composites are malleable and moldable, and can be formed or cut into the desired shape before and/or during implantation. For example, in one embodiment, the flexible composite can be cut into the desired size and/or shape using, e.g., a knife, shears, guillotine, or stamping with a die.

In one embodiment, the flexible composite is cut to the desired shape before implantation. In another embodiment, the flexible composite is molded into the desired shape during implantation. In another embodiment, the flexible composite is cut to a shape before implantation, and further molded during implantation.

Optionally, after fabrication, one or more surfaces of the flexible bone composites according to the invention may be treated to alter one or more chemical and/or physical properties of the one or more surfaces, e.g., to increase the surface hydrophilicity or to decrease the water contact angle. In one embodiment, the treatment can include exposure to an energy source capable of causing the one or more surfaces to become reactive, e.g., radiation such as gamma rays, plasma (using, e.g., gases such as oxygen, carbon dioxide, argon, ammonia, nitrogen, or the like, or a combination thereof), or the like, or combinations thereof, either by themselves or in combination with exposure to another reactive environment (e.g., presence of air, oxygen, ozone, or the like, exposure to chemically-reactive functional groups, or the like, or combinations thereof).

In one embodiment, one or more surfaces of the flexible bone composites according to the invention is treated with an oxygen plasma. In another embodiment, one or more surfaces of the flexible bone composites according to the invention is treated with a carbon dioxide plasma. In another embodiment, one or more surfaces of the flexible bone composites according to the invention is treated to form grafted surface(s) according to the HYDROLASTT™ process, commercially available from AST Industries, Inc., of Billerica, Mass., in which the one or more surfaces is exposed to a gas plasma such as oxygen, followed by reaction with a polymeric/oligomeric compound, e.g., a poly(alkylene oxide)/poly(alkylene glycol) such as PEO/PEG or a poly(alkylene imine) such as PEI.

Alternately or additionally, but also optionally, after fabrication, the flexible bone composites according to the invention may be aged, e.g., through prolonged exposure to degradatory means such as heat. In one embodiment, such optional processes can be performed, e.g., to alter the in vivo or in vitro degradation kinetics of the flexible bone composites according to the invention, or to attain a desired set of chemical and/or physical properties.

Figure 1:
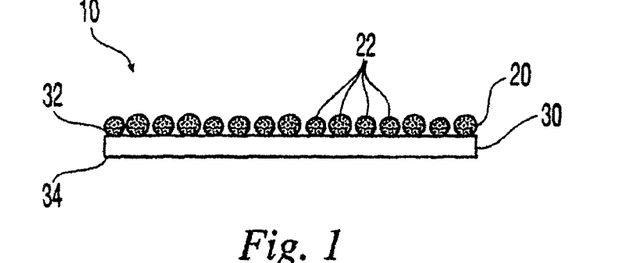
FIG. 1 depicts a cross-sectional view of an embodiment of the flexible bone composite of the invention having a polymeric layer and a calcium-containing layer.

FIGS. 1 to 6 show examples of embodiments of the flexible bone composite of the present invention where the calcium compound is in the form of granules. FIG. 1 depicts an exemplary flexible bone composite 10 of the invention having a polymeric layer 30 and a calcium-containing layer 20 including a calcium compound in the form of granules 22. The polymeric layer 30 has a first side 32 and a second side 34 and the granules 22 are affixed or physically and/or chemically attached to the first side 32 of the polymeric layer 30.

Figure 2:
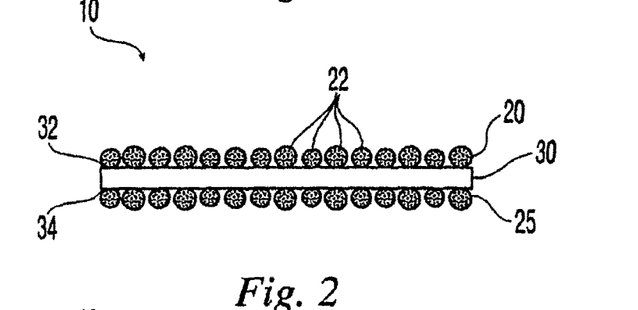
FIG. 2 depicts a cross-sectional view of an embodiment of a flexible bone composite of the invention having a first calcium containing layer, a polymeric layer, and second calcium-containing layer.

FIG. 2 depicts an embodiment of a flexible bone composite 10 having a first calcium-containing layer 20 including granules 22, a polymeric layer 30, and a second calcium-containing layer 25 including granules 22. As depicted in FIG. 2, the first calcium-containing layer 20 and second calcium-containing layer 25 are affixed or physically and/or chemically attached to the first side 32 and second side 34, respectively, of the polymeric layer 30.

Figure 3:
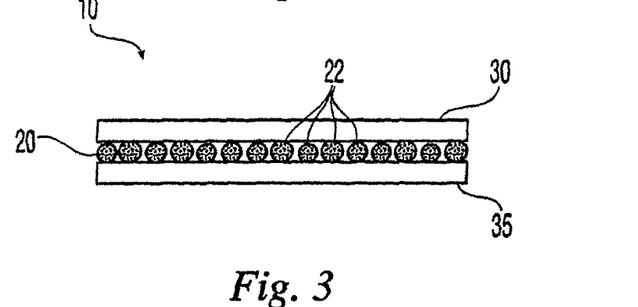
FIG. 3 depicts a cross-sectional view of an embodiment of a flexible bone composite of the invention having a first polymeric layer, a calcium-containing layer, and a second polymeric layer.

FIG. 3 depicts an embodiment of a flexible bone composite 10 of the invention having a first polymeric layer 30, a calcium-containing layer 20 including granules 22, and a second polymeric layer 35. As depicted in FIG. 3, the calcium-containing layer 20 is disposed between the first polymeric layer 30 and the second polymeric layer 35.

Figure 4A:
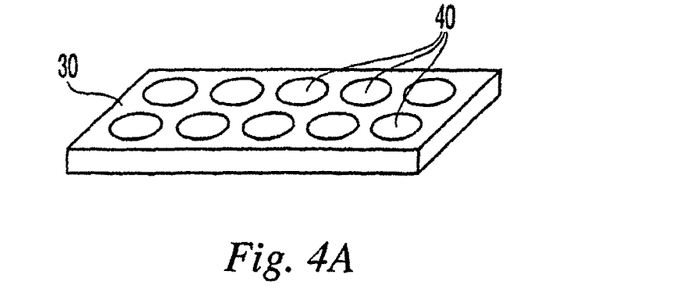
FIG. 4a depicts a perspective view of an embodiment of a polymeric layer of the invention, where the layer is perforated with holes.
Figure 4B:
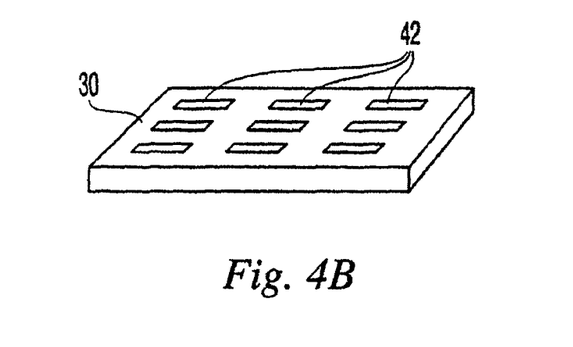
FIG. 4b depicts a perspective view of an embodiment of a polymeric layer of the invention, where the layer is perforated with slits.

FIGS. 4a and 4b depict embodiments of a polymeric layer 30 used in the flexible composite of the invention, wherein the polymeric layer 30 is perforated. In FIG. 4a, the perforations 40 in the polymeric layer 30 are substantially round. In FIG. 4b, the perforations 42 in the polymeric layer 30 are in the form of slits.

Figure 5:
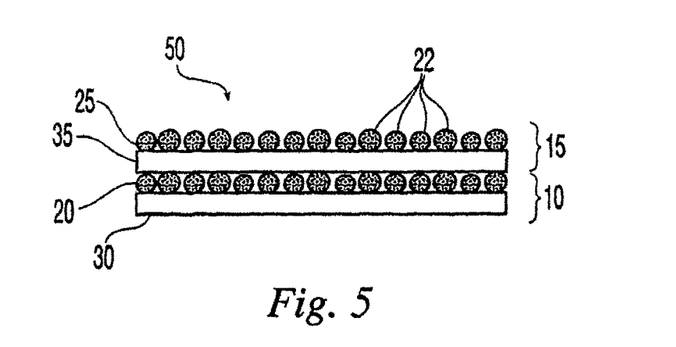
FIG. 5 depicts a cross-sectional view of a multilayer flexible bone composite of the invention having a first flexible bone composite and a second flexible bone composite.

FIG. 5 depicts a multilayer flexible bone composite 50 having a first composite 10 and a second composite 15 layered upon the first flexible bone composition 10. In FIG. 5, a multilayer flexible bone composite 50 is shown. The first composite 10 has a first polymeric layer 30 and a second calcium-containing layer 20 including granules 22 affixed or physically and/or chemically attached to one side of the polymeric layer 30; and a second composite 15 has a second polymeric layer 35 and a second calcium-containing layer 25 including granules 22 affixed or physically and/or chemically attached to one side of the polymeric layer 35.

Figure 6:
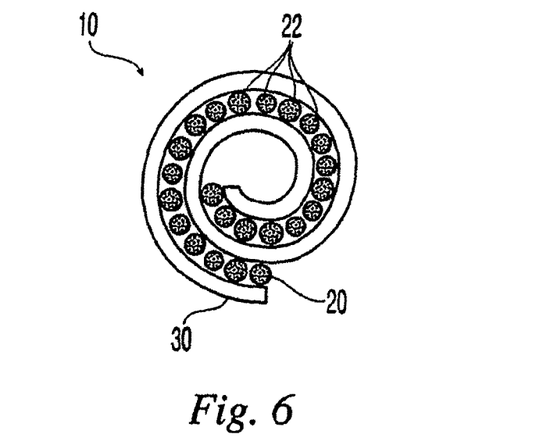
FIG. 6 depicts a cross-sectional view of an exemplary flexible bone composite of the invention having a polymeric layer and a calcium-containing layer, where the composite is rolled up.

FIG. 6 depicts an exemplary flexible bone composite 10 of the invention having a polymeric layer 30 and a calcium-containing layer 20 including granules 22 affixed or physically and/or chemically attached to one side of the polymeric layer 30, wherein the composite 10 is rolled up.

Optionally, a therapeutic substance such as, but not limited to, a chemical therapeutic substance and/or a biological therapeutic substance can be included in or on the flexible bone composite according to the invention. In one embodiment, these therapeutic substances can be present in or on the calcium-containing layer, the polymeric layer, or both. In another embodiment, the therapeutic substances can be added to the respective layers, can be impregnated within the layers, can be adhered to the surfaces of the layers, or can be included as a controlled release formulation within one or more of the layers. Non-limiting examples of the therapeutic substances include, but are in no way limited to, antimicrobials, antibiotics, chemotherapy drugs, growth factors (particularly osteoinductive growth factors) such as bone morphogenetic proteins, endothelial cell growth factors, insulin-like growth factors, or the like, or a combination thereof.

When the therapeutic substance is an antimicrobial agent, one, and usually no more than three, usually no more than two, antimicrobial agents may be present in the flexible bone composite. Non-limiting examples of useful antimicrobial agents include: Antiamebics, e.g. Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Diphetarsone, Emetine, Fumagillin, Glaucarubin, Glycobiarsol, 8-Hydroxy-7-iodo-5-quinoline-sulfonic Acid, Iodochlorhydroxyquin, Iodoquinol, Paromomycin, Phanquinone, Polybenzarsol, Propamidine, Quinfamide, Scenidazole, Sulfarside, Teclozan, Tetracycline, Thiocarbamizine, Thiocarbarsone, Timidazole; Antibiotics, e.g. Aminoglycosides (such as Amikacin, Apramycin, Arbekacin, Bambermycins, Butirosin, Dibekacin, Dihydrostreptomycin, Fortimicin(s), Gentamicin, Isepamicin, Kaniamycin, Micronomicin, Neomycin, Neomycin Undecylenate, Netilmicin, Paromomycin, Ribostamycin, Sisomicin, Spectinomycin, Streptomycin, Tobramycin, Trospectomycin), Amphenicols (Azidamfenicol, Chloramphenicol, Florfenicol, Thiamphenicol), Ansamycins (Rifamide, Rifampin, Rifamycin, Rifapentine, Rifaximin), .beta.-Lactams (Carbacephems, Loracarbef, Carbapenems (Biapenem, Imipenem, Meropenem, Panipenem), Cephalosporins (Cefaclor, Cefadroxil, Cefamandole, Cefatrizine, Cefazedone, Cefazolin, Cefcapene Povoxil, Cefclidin, Cefdinir, Cefditoren, Cefepime, Cefetamet, Cefixime, Cefinenoxine, Cefodizime, Cefonicid, Cefoperazone, Ceforanide, Cefotaxime, Cefotiam, Cefozopran, Cefpimizole, Cefpiramide, Cefpirome, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin), Cephamycins (Cefbuperazone, Cefmetazole, Cefminox, Cefotetan, Cefoxitin), Monobactams (Aztreonam, Carumonam, Tigemonam), Oxacephens (Flomoxef, Moxalactam), Penicillins (Amdinocillin, Amdinocillin Pivoxil, Amoxicillin, Ampicillin, Apalcillin, Aspoxicillin, Azidocillin, Azlocillin, Bacampicillin, Benzylpenicillic Acid, Benzylpenicillin Sodium, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Naacillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin 0, Penicillin V, Penicllin V Benzathine, Penicillin V Hydrabamine, Penimepicycline, Phenethicillin Potassium, Piperacillin, Pivampicillin, Propicillin, Quinacillin, Sulbenicillin, Sultamicillin, Talampicillin, Temocillin, Ticarcillin), Ritipenem), Lincosamides (Clindamycin, Lincomycin), Macrolides (Azithromycin, Capbomycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin), Polypeptides (Amphomycin, Bacitracin, Capreomycin, Colistin, Enduracidin, Enviomycin, Fusafungine, Gramicidin S, Gramicidin(s), Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin), Tetracyclines(Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Tetracycline), Cycloserine, Mupirocin, Tuberin; synthetic antibacterial agents, e.g. 2,4-Diaminopyrimidines (Brodimoprim, Textroxoprim, Trimethoprim), Nitrofurans (Furaltadone, Furazolium Chloride, Nifuradene, Nifuratel, Nifurfoline, Nifurpirinol, Nifurprazine, Nifurtoinol, Nitrofirantoin), Quinolones and Analogs (Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nadilixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin), Sulfonamides (Acetyl Sulfamethoxpyrazine, Benzylsulfamide, Chloramine-B, Chloramine-T, Dichloramine T, $N_2$-Formylsulfisomidine, $N_4$-β-D-Glucosylsulfanilamide, Mafenide, 4'-(Methylsulfamoyl)sulfanilanilide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, 4-Sulfanilamidosalicylic Acid, $N_4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole), Sulfones (Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, Sulfoxone Sodium, Thiazolsulfone), Clofoctol, Hexedine, Methenamine, Methenamine Anhydromethylenecitrate, Methenamine Hippurate, Methenamine Mandelate, Methenamine Sulfosalicylate, Nitroxoline, Taurolidine, Xibomol; leprostatic antibacterial agents, such as Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium, antifungal agents, such as Allylamines Butenafine, Naftifine, Terbinafine, Imidazoles (e.g., Bifonazole, Butoconazole, Cholordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole Nitrate, Sertaconazole, Sulconazole, Tioconazole), Thiocarbamates (Tolcilate, Tolindate, Tolnaftate), Triazoles (Fluconazole, Itraconazole, Saperconazole, Terconazole), Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, Zinc Propionate; and the like.

Other antimicrobial agents useful in the present invention include Q-lactamase inhibitors (e.g. Clavulanic Acid, Sulbactam, Tazobactam); Chldramphenicols (e.g. Azidamphenicol, Chloramphenicol, Thiaphenicol); Fusidic Acid; synthetic agents such as Trimethoprim, optionally in combination with sulfonamides) and Nitroimidazoles (e.g., Metronidazole, Timidazole, Nimorazole); Antimycobacterial agents (e.g. Capreomycin, Clofazimine, Dapsone, Ethambutol, Isoniazid, Pyrazinamide, Rifabutin, Rifampicin, Streptomycin, Thioamides); Antiviral agents (e.g. Acryclovir, Amantadine, Azidothymidine, Ganciclovir, Idoxuridine, Tribavirin, Trifluridine, Vidarabine); Interferons (e.g. Interferon α, Interferon β); and antiseptic agents (e.g., Chlorhexidine, Gentian violet, Octenidine, Povidone Iodine, Quaternary ammonium compounds, Silver sulfadiazine, Triclosan).

The therapeutic substance can further include a biological therapeutic substance, such as, e.g., a protein. In one embodiment, bone associated proteins may be added to modify the physical properties of the composition, enhance resorption, angiogenesis, cell entry and proliferation, mineralization, bone formation, growth of osteoclasts and/or osteoblasts, or the like. Proteins of particular interest are the different types of collagen, particularly Type 1. Other proteins include osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenic proteins (e.g., BMP-1, -2A, -2B, -3, -3b, -4, -5, -6, -7, -8, -8b, -9, -10, -11, -12, -13, -14, -15), cartilage induction factor, platelet derived growth factor (PDGF-1, -2), endothelial cell growth factors (ECGF-1, -2a, -2b), skeletal growth factor (SKF=IGF-2), insulin-like growth factors (IGF-1, IGF-2), fibroblast growth factor (ODGF-1, -2, -3, -4, -5, -6, -7, -8, -9, -10, -11, -12, -13, -14, -15, -16, -17, -18, -19, -20, -21, -22, -23), colony stimulating factor, transforming growth factor (e.g., TGF-(3), vascular endothelial growth factors (VEGF), growth/differentiation factors (GDF-1, -3, -5, -6, -7, -8, -9, -9B, -10, -11, -15, -16), osteogenic proteins (OP-1=BMP-7, OP-2=BMP-8, OP-3=BMP-8b), bone growth hormone, parathyroid hormone (PTH), insulin, calcitonin, and the like. The proteins can also include proteins associated with cartilage, such as chondrocalcining protein; proteins associated with dentin, such as phosphophoryn, glycoproteins and Gla proteins; or proteins associated with enamel, such as amelognin and enamelin. Structural proteins of interest for use in the present invention include, but are not limited to, fibrin, fibrinogen, keratin, tubulin, elastin, and the like. In one embodiment, blood proteins may be employed, individually or together, in plasma or serum, e.g., serum albumin.

In some embodiments, the therapeutic substance can further include a non-protein growth factor such as prostaglandins and statins (e.g., Simvastatin, Lovastatin).

In one embodiment, the therapeutic substance is a growth factor such as, but not limited to, bone morphogenetic proteins, endothelial cell growth factors, insulin-like growth factors, or the like, or a combination thereof.

Any suitable amount of therapeutic substance may be used. For example, the amount of antimicrobial agent that is present in the flexible bone composite may be an amount sufficient to provide for a product that at least reduces the growth rate of microbial organisms in the region of the product as compared to a control. In many embodiments, the amount of antibiotic will be sufficient to provide for a zone of inhibition having a diameter of at least about 10 mm, usually at least about 15 mm, as measured by the antibiotic activity assay as described U.S. Pat. No. 5,968,253 to Poser et al., the entire content of which is expressly incorporated herein by reference. The amount of therapeutic substance used in the flexible bone composite can vary depending on factors such as location of the repair, age and health of the patient, and the like, and can be determined by one skilled in the art.

Flexible bone composites including a therapeutic substance are also useful in the local delivery of such substance, e.g. to a physiological site of interest. For example, flexible bone composites including an antimicrobial agent are useful for methods requiring release of an antimicrobial agent into a local environment over an extended period of time, where the period of time is generally at least about 5, usually at least about 10, and more usually at least about 20 days, where the flexible bone composites may release the antimicrobial agent into their local environment for as long as 40 days or longer, depending on the specific composition from which the product is prepared. Thus, the flexible bone composites including an antimicrobial agent find use as extended antimicrobial agent delivery vehicles, i.e. as antimicrobial agent depots, in which the local delivery of an antimicrobial agent for an extended period of time is desired. The subject compositions find particular use as local antimicrobial agent delivery vehicles for bone tissue, particularly cancellous bone tissue.

In addition to, or instead of, therapeutic substances, flexible bone composites according to the invention can contain cells, particularly mononuclear cells, e.g., that are or can be differentiated (in vivo) into cells related to bone (i.e., osteogenic cells, precursors, or associated materials such as osteoblasts, osteoblast precursors, bone marrow cells, blood cells, connective tissue cells including smooth muscle cells and the like, connective tissue progenitors, mesenchymal stem cells, collagen, fibrin, or the like, or a combination thereof). Flexible bone composites containing such cells, whether on the surface(s) or in the interior, can advantageously be used as a matrix for tissue engineering.

When utilized, the cells, whether allogenic, autogenic, or xenogenic, can be harvested and/or isolated by any known or conventional means, e.g., by centrifugation of bone marrow to isolate mononuclear cells, followed, for instance, by cell seeding and culturing in an osteogenic medium.

The invention also includes methods for making a flexible bone composite including a polymeric layer and a calcium-containing layer.

The flexible bone composite can be made by forming a polymeric layer as described above, and depositing a first calcium compound on the first side of the polymeric layer to form a first calcium-containing layer on the polymeric layer. Any suitable method for affixing or physically and/or chemically attaching the calcium compound to the surface of the first side of the polymeric layer can be used. For example, in one embodiment, the calcium compound can be affixed or physically and/or chemically attached to the first side of the polymeric layer by heating the polymeric layer for a time and a temperature sufficient to cause the calcium compound disposed on the surface of the first polymeric layer to physically and/or chemically attach to or adhere to the surface, e.g., by heating the polymeric layer until it becomes tacky. In another non-limiting embodiment, the calcium compound is affixed or physically and/or chemically attached to the surface of a gel (which forms the first polymeric layer) to form a calcium-containing layer on the first polymeric layer. Optionally, the method of affixing or of physically and/or chemically attaching the calcium compound to the polymeric layer can include applying pressure.

In one embodiment, the flexible bone composite is made by forming a polymeric layer having a first side and a second side; contacting a first calcium compound with the first side of the polymeric layer to form a first intermediate composite; and heating the first intermediate composite at a temperature sufficient to affix or to physically and/or chemically attach the first calcium compound to the first side of the polymeric layer.

In one embodiment, the polymeric layers of the invention can be perforated prior to contact with the calcium compound.

In another embodiment, the invention includes a method for making a flexible bone composite including a perforated polymeric layer having a first side and a second side, including: perforating a polymeric layer to form a perforated polymeric layer; heating the perforated polymeric layer; contacting a first calcium compound with the first side of the perforated polymeric layer to form a first intermediate composite; and allowing the first intermediate composite to cool to a temperature sufficient to affix or to physically and/or chemically attach the first calcium compound to the first side of the perforated polymeric layer to provide a first calcium-containing layer.

In one embodiment, the perforated polymeric layer is heated for a time and a temperature sufficient to make the polymeric layer tacky.

Another method for making a flexible bone composite includes: casting a solution including a polymer and a solvent onto a release surface; allowing the solution to form a gel; contacting a calcium compound with a first side of the gel; and allowing the solvent to evaporate from the gel to form a flexible bone composite having a calcium-containing layer affixed or physically and/or chemically attached to the first side of the polymeric layer.

Once prepared, the flexible bone composite may be dried under reduced pressure, packaged within an appropriate moisture and sterilized.

Another aspect of the present invention includes a kit or packaging system for storing, preparing, mixing, and/or administering composites according to the invention.

The flexible bone composites according to the present invention can be used as or in implantable medical devices, and the like. Specifically, such applications or devices can include, but are not limited to, bone graft containment (e.g., bone graft or bone graft substitutes) or bone void filler either alone or in combination with one or more other conventional devices, which can include, but are not limited to, bone fixation plates (e.g., craniofacial, maxillofacial, orthopedic, skeletal, or the like); screws, tacks, clips, staples, nails, pins or rods, anchors (e.g., for suture, bone, or the like); scaffolds, scents, meshes (e.g., rigid, expandable, woven, knitted, weaved, etc.); sponges, implants for cell encapsulation or tissue engineering, drug delivery (e.g., carriers, bone ingrowth induction catalysts such as bone morphogenetic proteins, growth factors, peptides, and the like, antivirals, antibiotics, etc.); monofilament or multifilament structures, sheets, coatings, membranes (e.g., porous, microporous, resorbable, etc.); foams (e.g., open cell or closed cell), screw augmentation, cranial reconstruction; and/or combinations thereof. When used in or with implantable medical devices, the flexible bone composite is preferably bioabsorbable and/or resorbable.

Any method for implanting the flexible bone composite can be used. For example, in one embodiment, the flexible bone composite can be laid into a void, placed onto a bone or bones, rolled and packed into a void, folded and packed into a void, and the like.

In one embodiment, the invention includes a method for treating a hard tissue defect, e.g., bone or cartilage, in a patient in need thereof, including implanting a therapeutically effective amount of the flexible bone composite of the invention into the defect. Such bone defects include, but are not limited to, bone void, bone grafts, spine defects, an orthopedic defects, or maxillofacial defects. In one embodiment, the bone defect is a bone void.

In another embodiment, the invention includes a method for treating a bone defect further including using a fixation device with the flexible composite. Non-limiting examples of fixation devices include plates, screws, tacks, pins, rods, vertebral spacers, or any combination thereof.

In another embodiment, the invention includes methods for aspirating bone marrow in a patient in need thereof, including: implanting a therapeutically effective amount of the flexible bone composite into an area proximal to the bone marrow. For example, in one embodiment, the flexible bone composite can be soaked in aspirated bone marrow and implanted as described above.

EXAMPLES

Preferred embodiments of the present invention and comparative embodiments will be illustrated by reference to the following examples, which are included to exemplify, but in no way limit, the scope of the present invention.

Example 1

About 2.94 g of 70:30 poly(L-lactide-co-ε-caprolactone) (PURASORB®, by Purac, Lincolnshire, Ill.) having an intrinsic viscosity of about 1.5 dl/g was compression molded into a film using a Carver Compression Press, Model No. 3895 (Carver, Inc., Wabash, Ind.) by placing the polymer between stainless steel shims (about 0.12 mm) sprayed with Price-Driscoll anti-stick mold release (Price-Driscoll Corp., Waterford, Conn.), and using about 0.11 mm brass shims to control the polymer thickness and using the following compression conditions: platen set point temperature, about 150° C.; load, about 10,000 kg; pump, about 80%; dwell time, about 50 sec. After compression, the film was cooled on a cold plate to provide a polymeric layer having a thickness of about 0.10 to about 0.12 mm.

Example 2

A polymeric layer was prepared from about 2.99 g of 70:30 poly(L-lactide-co-ε-caprolactone) as described in Example 1, except that Kapton® polyimide release sheets (DuPont, Wilmington, Del.) (about 1 mil thick) were placed between the polymer and the stainless steel shims. The resultant polymer film released easily from the sheets after cooling with cold air to provide a polymeric layer having a thickness of about 0.15 to about 0.18 mm and a diameter of 130 mm.

Example 3

A polymeric layer was prepared from about 2.96 g of 70:30 poly(L-lactide-co-ε-caprolactone) as described in Example 2, except that the load was about 15,000 kg, and the dwell time was about 60 sec. The resultant polymer film had a thickness of about 0.13 to about 0.15 mm and a diameter of about 143 mm.

Example 4

A polymeric layer was prepared from about 2.95 g of 70:30 poly(L-lactide-co-ε-caprolactone) as described in Example 3, except that the load was about 20,000 kg. The resultant polymeric layer exhibited bubbles, which was attributed to too thin a spread of polymer during setup. The polymeric layer had a thickness of about 0.13 to about 0.14 mm and a diameter of about 146 mm.

Example 5

A polymeric layer was prepared from about 2.97 g of 70:30 poly(L-lactide-co-ε-caprolactone) as described in Example 3, except that the platen set point was about 158° C. and the load was about 20,000 kg. The resultant polymer film had a thickness of about 0.11 to about 0.14 mm and a diameter of about 149 mm.

Example 6

A polymeric layer was prepared from about 2.95 g of 70:30 poly(L-lactide-co-ε-caprolactone) as described in Example 1, except that the platen set point was about 160° C., the load was about 24,000 kg, and the dwell time was about 70 sec. The resultant polymeric layer had a thickness of about 0.11 to about 0.13 mm and a diameter of about 150 mm.

Example 7

A polymeric layer was prepared from about 3.40 g of 70:30 poly(L-lactide-co-ε-caprolactone) as described in Example 6. The resultant polymeric layer had a thickness of about 0.11 to about 0.13 mm and a diameter of about 160 mm.

Example 8

A polymeric layer was prepared from about 3.43 g of 70:30 poly(L-lactide-co-ε-caprolactone) as described in Example 7 except that the dwell time was 75 sec. The resultant polymeric layer had a thickness of about 0.11 to about 0.13 mm and a diameter of about 160 mm.

Example 9

A polymeric layer was prepared from about 3.40 g of 70:30 poly(L-lactide-co-ε-caprolactone) as described in Example 8 to provide a polymeric layer having a thickness of about 0.11 to about 0.13 mm and a diameter of about 160 mm.

Example 10

A polymeric layer was prepared from about 3.51 g of 70:30 poly(L-lactide-co-ε-caprolactone) as described in Example 7 to provide a polymeric layer having a thickness of about 0.11 to about 0.13 mm and a diameter of about 160 mm.

Example 11

A polymeric layer was prepared from about 3.49 g of 70:30 poly(L-lactide-co-ε-caprolactone) as described in Example 7 to provide a polymeric layer having a thickness of about 0.11 to about 0.13 mm and a diameter of about 160 mm.

Example 12

Polymeric strips of 70:30 poly(L-lactide-co-ε-caprolactone) copolymer (thickness, about 0.1 mm; width, about 10 mm) were prepared according to Example 7 and placed in a phosphate buffer solution (about pH 7.4) maintained at about 37° C. Strips were removed from the buffer and their tensile strengths were determined. See the results in Table 1.

TABLE 1

Changes in tensile strength for a 70:30 poly(L-lactide-co-ε-caprolactone) copolymer maintained in a phosphate buffer solution (pH ~7.4).

| Weeks | Tensile Strength Peak (MPa) | Yield Strength 0.2% Offset (MPa) | Modulus (MPa) |
|---|---|---|---|
| 0 | 42.4 | 10.8 | 360.9 |
| 2 | 30.0 | 7.6 | 141.0 |

TABLE 1-continued

Changes in tensile strength for a 70:30 poly(L-lactide-co-ε-caprolactone) copolymer maintained in a phosphate buffer solution (pH ~7.4).

| Weeks | Tensile Strength Peak (MPa) | Yield Strength 0.2% Offset (MPa) | Modulus (MPa) |
|---|---|---|---|
| 4 | 27.8 | 7.1 | 133.9 |
| 8 | 15.7 | 6.5 | 147.9 |
| 12 | 5.2 | 3.8 | 117.9 |

Example 13

A polymeric layer of a 60:14:26 poly(glycolide-co-dioxanone-co-trimethylene carbonate) was prepared as described in Example 2, except the platen set point temperature was about 160° C., the load was about 24,000 kg, and the dwell time was about 70 sec.

Example 14

Polymeric strips of the 60:14:26 poly(glycolide-co-dioxanone-co-trimethylene carbonate) copolymer of Example 13 (diameter, about 0.1 mm; width, about 10 mm) were placed in a phosphate buffer solution (about pH 7.4) maintained at about 37° C. Strips were removed from the buffer and their tensile strengths were determined. The results are shown in Table 2.

TABLE 2

Changes in tensile strength for a 60:14:26 poly(glycolide-co-dioxanone-co-trimethylene carbonate)copolymer maintained in a phosphate buffer solution (pH 7.4).

| Weeks | Tensile Strength Peak (MPa) | Yield Strength 0.2% Offset (MPa) | Modulus (MPa) |
|---|---|---|---|
| 0 | 62.1 | 16.4 | 355.7 |
| 1 | 49.5 | 16.9 | 352.6 |
| 2 | 23.9 | 15.1 | 412.0 |

Example 15

The polymeric layer of Example 11 was perforated by placing the polymeric layer over a soft substrate and punching about 1/16" (1.5875 mm) holes approximately 4-5 mm apart in the polymeric layer using a 1/16" punch and a mallet. The resultant perforated polymeric layer was placed between layers of a $\beta$-$Ca_3(PO_4)_2$ (available from Synthes, Paoli, Pa. under the tradename chronOS™) and having a diameter of about 1.4 to about 2.8 mm. The layered composition was placed in a stainless steel mold, and the mold was held together with medium paper binders. The mold was placed in a convention oven at about 130° C. for about 15 minutes to provide a flexible bone composite having a perforated resorbable polymeric layer.

Example 16

A flexible bone composite was prepared as described in Example 15, except the polymeric layer was not perforated and the mold was heated in a convection oven at about 140° C.

Example 17

A flexible bone composite was prepared as described in Example 16, except the polymeric layer was slit (about 2 to about 3 mm in length) with a scalpel about 4-5 mm apart.

Example 18

A flexible bone composite was prepared as described in Example 15, except the chronOS™ granules had a diameter of about 0.5 to about 0.7 mm, and the mold was heated in a convection oven at about 145° C. for about 20 minutes.

Examples 19-22

Effect of Surface Treatment on Composite Blood Uptake

Four types of flexible bone composites according to the invention were fabricated in the same general manner as in Example 18 (but with the diameter of polymeric layer from Example 11 being about 250 mm, the thickness of the polymeric layer varying from about 0.09 to about 0.17 mm, and with the polymer weight exhibiting a change commensurate with the increased diameter) and were annotated as Examples 19-22. The composite of Example 19 contained a surface that was native, or untreated, while the surfaces of composites of Examples 20-22 were treated so as to make them more hydrophilic through exposure to oxygen plasma, to carbon dioxide plasma, and to a HYDROLAST™ treatment (which is a plasma/grafting treatment process commercially available from AST Products, Inc., of Billerica, Mass., and which is described, inter alia, in U.S. Pat. Nos. 5,700,559, 5,807,636, and 5,837,377, the entire disclosures of which are hereby incorporated by reference), respectively. The conditions for the oxygen and carbon dioxide plasma treatments were similar to those used in the plasma portion of the HYDROLAST™ treatment process, which in these cases included RF plasma at a pressure of about 30 milliTorrs and at a power of about 250 Watts.

For each of the Examples 19-22, some flexible bone composites were used as fabricated, while others were aged for about 21 days at about 45° C. The flexible bone composites of Examples 19-22, both as-fabricated and aged, were soaked in bovine blood under ambient conditions for about 30 seconds to determine blood uptake levels. Table 3 below shows the results. Mean uptake values represent the average of experiments on about 15 separate samples.

TABLE 3

Bovine blood uptake for flexible bone composites according to the invention - treated vs. untreated and aged vs. as-fabricated.

| Example | Treatment | Aged | Mean Uptake |
|---|---|---|---|
| 19 | None | Y | 54% |
|  |  | N | 51% |
| 20 | $O_2$ plasma | Y | 68% |
|  |  | N | 64% |
| 21 | $CO_2$ plasma | Y | 59% |
|  |  | N | 61% |
| 22 | HYDROLAST ™ | Y | 64% |
|  |  | N | 69% |

Although the present invention is described with reference to certain preferred embodiments, it is apparent that modification and variations thereof can be made by those skilled in the art without departing from the scope or this invention, particularly as defined by the appended claims.

What is claimed is:

1. A multilayer flexible bone composite comprising:
a first polymeric layer comprising a flexible polymer and having a first side and a second side;

a first calcium-containing layer comprising granules of a calcium compound affixed to the first side of the first polymeric layer, wherein a majority of the external surface of the granules of the first calcium-containing layer is not covered with polymer; and a second calcium-containing layer comprising granules of a calcium compound affixed to the second side of the first polymeric layer.

2. The multilayer flexible bone composite of claim 1, further including a second polymeric layer comprising a flexible polymer, wherein the second calcium-containing layer is disposed between the first polymeric layer and the second polymeric layer.

3. The multilayer flexible bone composite of claim 2, wherein the second polymeric layer has a first side and a second side and wherein the granules of the second calcium-containing layer are affixed to the first side of the second polymeric layer.

4. The multilayer flexible bone composite of claim 2, wherein the first polymeric layer and/or the second polymeric layer is substantially free of calcium compounds.

5. The multilayer flexible bone composite of claim 2, wherein the first polymeric layer and/or the second polymeric layer comprises a resorbable polymer.

6. The multilayer flexible bone composite of claim 2, wherein the first polymeric layer and/or the second polymeric layer comprises a synthetic polymer.

7. The multilayer flexible bone composite of claim 2, wherein the flexible polymer of the first polymeric layer and/or the second polymeric layer comprises repeat units selected from the group consisting of L-lactic acid, D-lactic acid, L-lactide, D-lactide, D,L-lactide, glycolide, a lactone, a lactam, $\epsilon$-caprolactone, trimethylene carbonate, a cyclic carbonate, a cyclic ether, para-dioxanone, beta-hydroxybutyric acid, beta-hydroxypropionic acid, beta-hydroxyvaleric acid, and combinations thereof.

8. The multilayer flexible bone composite of claim 2, wherein the flexible polymer of the first polymeric layer and/or the second polymeric layer has a glass transition temperature between about 30 degrees C. and about 100 degrees C.

9. The multilayer flexible bone composite of claim 2, wherein the first polymeric layer and/or the second polymeric layer has a thickness ranging from about 0.01 mm to about 1.0 mm.

10. The multilayer flexible bone composite of claim 2, wherein the first polymeric layer and/or the second polymeric layer includes one or more perforations.

11. The multilayer flexible bone composite of claim 2, wherein the first polymeric layer and/or the second polymeric layer includes one or more cuts or slits.

12. The multilayer flexible bone composite of claim 11, wherein the one or more cuts or slits has a length ranging from about 0.5 mm to about 10 mm.

13. The multilayer flexible bone composite of claim 1, wherein first calcium-containing layer and/or the second calcium-containing layer is substantially free of polymer.

14. The multilayer flexible bone composite of claim 1, wherein the calcium compound of the first calcium-containing layer and/or the second calcium-containing layer are selected from the group consisting of $CaHPO_4 \cdot nH_2O$, $\alpha\text{-}Ca_3(PO_4)_2$, $\alpha\text{-bar-}Ca_3(PO_4)_2$, $\beta\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $Ca_2P_2O_7$, $Ca(H_2PO_4)_2 \cdot nH_2O$, $Ca_8H_2(PO_4)_6 \cdot nH_2O$, and combinations thereof, where n is a number ranging from 0 to 5.

15. The multilayer flexible bone composite of claim 1, wherein the calcium compound of the first calcium-containing layer and the second calcium-containing layer is $\beta\text{-}Ca_3(PO_4)_2$.

16. The multilayer flexible bone composite of claim 1, wherein the calcium compound of the first calcium-containing layer and/or the second calcium-containing layer is substantially free of hydroxyapatite.

17. The multilayer flexible bone composite of claim 1, wherein the granules of the first calcium-containing layer and/or the second calcium-containing layer have a mean diameter of about 0.05 mm to about 10 mm.

18. The multilayer flexible bone composite of claim 1, wherein each granules of the first calcium-containing layer and/or the second calcium-containing layer has a surface area of about 0.1 m$^2$/g to about 100 m$^2$/g.

19. The multilayer flexible bone composite of claim 1, further comprising bone marrow cells in an interior of the multilayer flexible bone composite prior to implantation.

20. The multilayer flexible bone composite of claim 1, wherein the multilayer flexible bone composite is soaked in aspirated bone marrow.

* * * * *